United States Patent [19]

Wiley

[11] 4,345,075

[45] Aug. 17, 1982

[54] 4-AMINO-6-(2'-CARBOXYETHYL)-3-METHYLTHIO-1,2,4-TRIAZIN-5(4H)-ONE

[76] Inventor: Richard H. Wiley, 8 Roosevelt Cir., Palo Alto, Calif. 94306

[21] Appl. No.: 300,906

[22] Filed: Sep. 10, 1981

[51] Int. Cl.³ .................................................. C07D 253/06
[52] U.S. Cl. ................................................... 544/182
[58] Field of Search .......................................... 544/182

[56] References Cited

U.S. PATENT DOCUMENTS

| | | | |
|---|---|---|---|
| 3,671,523 | 6/1972 | Westphal et al. | 544/182 |
| 3,905,801 | 9/1975 | Fawzi | 544/182 X |
| 3,961,936 | 6/1976 | Westphal et al. | 544/182 X |
| 4,036,632 | 7/1977 | Westphal et al. | 71/93 |
| 4,058,525 | 11/1977 | Hofer et al. | 544/182 |
| 4,252,944 | 2/1981 | Wiley | 544/182 |

Primary Examiner—John M. Ford

[57] ABSTRACT

4-Amino-6-(2'carboxyethyl)-3-methylthio-1,2,4-triazin-5(4H)-one is prepared by reaction of methylthiocarbonohydrazide iodide with α-ketoglutaric acid for use as a previously unknown compound in structure-activity relationship studies of herbicides and plant growth regulators and as an intermediate in the preparation of new 1,2,4-triazin-5(4H)-ones.

1 Claim, No Drawings

4-AMINO-6-(2'-CARBOXYETHYL)-3-METHYLTHIO-1,2,4-TRIAZIN-5(4H)-ONE

BACKGROUND

6-Alkyl- and aryl-4-amino-3-methylthio-1,2,4-triazin-5(4H)-ones are known (Dornow, Chem. Ber. 1964, 2173; U.S. Pat. Nos. 3,671,523; 3,961,936; 3,966,715; and 4,113,767) and one member of the class; i.e., the 6-tert.-butyl compound, is the widely used herbicide, metribuzin (Merck Index No. 6027). A variety of substituted types are known which possess herbicidal activity. 6-Carboxy and 6-(δ-carboxyalkyl)-3-mercapto-4-amino-1,2,4-triazin-5(4H)-ones are described in my copending application Ser. No. 06/238,480 filed 02/26/81. These 6-carboxyalkyl types are advantageously obtained from α-keto dicarboxylic acids thus avoiding the costly economic and environmental problems encountered in the manufacture of the 6-tert.-butyl derivative, metribuzin. These problems have been stated in detail in U.S. Pat. No. 4,113,767, which describes a sulfur dichloride chlorination process for the preparation of trimethylpyruvic acid, the primary starting material - a process which is a source of contaminating possibilities such as the chlorinated by-products resulting from sulfur dichloride chlorination of the tert.-butyl group. α-Ketoglutaric acid, the starting material for the preparation of the 6-(2'-carboxyethyl)-triazinone of the present invention is available from environmentally acceptable and economically advantageous fermentation processes (U.S. Pat. Nos. 2,443,919; 2,841,616).

3-Methylthio-triazin-5(4H)-ones have been previously and customarily prepared by reaction of a strongly alkaline solution of the 6-mercaptotriazinone with methyl iodide (U.S. Pat. Nos. 4,113,767; 4,036,622). There is no known previous reference to the use of S-methylthiocarbonohydrazide iodide, the preparation which is given in J. Org. Chem. 19, 1231 (1954), for the preparation of 3-methylthio-4-amino-6-substituted-1,2,4-triazin-5(4H)-ones of any type.

Description of the Invention

4-Amino-6-(2'-carboxyethyl)-3-methylthio-1,2,4-triazin-5(4H)-one is prepared from S-methylthiocarbonohydrazide and α-ketoglutaric acid. The S-methylthiocarbonohydrazide in the form of a quaternary salt is dissolved in a suitable solvent at slightly elevated temperature and mixed at once with an approximately equivalent amount of the α-keto dicarboxylic acid to form a warm solution from which the product precipitates in good yield and in essentially pure format once or on standing and cooling. The S-methylthiocarbonohydrazide is used in the form of its iodide salt prepared as described in J. Org. Chem. 19, 1231 (1954).

The solvent used in the reaction is water or alcohol-water. The use of water alcohol mixtures increases the yield by decreasing the solubility of the product and facilitating its isolation. The amount of alcohol used is selected as less than that at which ready solution of the reactants can be obtained.

The reaction is run at temperatures of 50°-100° C. preferably at 60°-70° C. At lower temperatures the reactants are not readily soluble and thus are less available for complete and prompt reaction. At higher temperature the α-keto acid undergoes slight decarboxylation with resultant lowering of the yield of product. The reaction at 60°-70° C. is rapid and immediately on or within minutes after mixing the product begins to precipitate. Additional time is allowed for completion of the reaction. The order of mixing of the reactants is not critical but it is advantageous to first dissolve the S-methylthiocarbonohydrazide and then dissolve the acid thus minimizing loss of acid through decarboxylation.

The yield of product is enhanced by partial evaporation of the reaction mixture before or after separation of the initially precipitated product. The by-product hydrogen iodide can be recovered for reuse from the mother liquor—as methyl iodide.

A remarkable feature of this invention is that it circumvents the usual procedure for the conversion of 3-mercaptotriazinones to their S-methyl derivatives. The usual and customary procedure utilizes the reaction of the mercaptotriazinone with methyl iodide in the presence of an equivalent amount of strong base; e.g., sodium methoxide or hydroxide in methanol or dimethylformamide. Such strongly alkaline conditions are inoperable for converting the mercapto-carboxy-triazinone to its S-methyl derivative. The acid must be neutralized to achieve the requisite alkalinity and the resultant carboxylate anion is readily decarboxylated or disruptive of the displacement reaction or has altered solubility characteristics making isolation of the product difficult.

The product of the invention is isolated in an essentially pure form. It can, however, be further purified by washing with cold alcohol or ether, in which it is insoluble or by recrystallization from hot alcohol in which it is sparingly soluble or from hot alcohol with small amounts of added water. The product is acidic and can be titrated with standard base. Potentiometric titration shows a pronounced break at an equivalence point near pH 8.5 and a pH at half neutralization of about 5 indicating a $pK_a$ in the 5 range.

The following examples illustrate the operation of the invention.

EXAMPLE 1

4-Amino-6-(2'-carboxyethyl)-3-methylthio-1,2,4-triazin-5(4H)-one. To 20 ml of water at 60° C. is added 10.8 g (0.0435 moles) of S-methylthiocarbonohydrazide iodide. After stirring briefly to dissolve, 6.0 g (0.04 moles) of α-ketoglutaric acid are added. The mixture is stirred to solution and warmed to 70° C. within a few minutes and then allowed to cool. On standing, or more rapidly if seeded, at room temperature (or in an ice bath) crystals of the product separate. The crystals are collected, washed with cold water, then with cold ethanol, and dried to give 3.8 g of product, mp 203°-204° C. (dec.). The reaction mixture after filtration is diluted with an equal volume of ethanol to precipitate an additional 3 g of product. The total yield is 74% of theory. The product is soluble in hot water, hot ethanol, hot methanol, and in 2 N sodium hyroxide. The analytical sample is dried at 55° C./0.5 mm.

Anal. Calcd. for $C_7H_{10}O_3N_4S$: C, 36.52; H, 4.35; N, 24.35; S, 13.91; neutr. equiv., 230. Found: C, 36.49; H, 4.60; N, 23.93; S, 13.88; neutr. equiv., 230.1 (potentiometric; to pH 8.5 at equivalence).

EXAMPLE 2

Example 1 is repeated using 1.25 N hydrochloric acid in place of the water. The product is obtained in low yield.

EXAMPLE 3

Example 1 is repeated with the temperature being raised to, at first 90° C., at which temperature gas evolution ($CO_2$) is noted, and then to 95° C. The yield of product is low and the product is contaminated with the carbohydrazone.

The product of this invention is useful in further delineating the structure-activity relations amongst herbicides of the triazinone type and plant growth regulators of the auxin type. The product shows injury to several weed species in post-emergence tests. The product is also useful as an intermediate in the preparation of previously undesribed, novel herbicides and plant growth regulators via conversion of the carboxylic acid group.

I claim:
1. 4-Amino-6-(2'-carboxyethyl)-3-methylthio-1,2,4-triazin-5(4H)-one.